United States Patent [19]

Frollini, Jr. et al.

[11] Patent Number: 4,608,148

[45] Date of Patent: Aug. 26, 1986

[54] COMBINATION PH/REFERENCE ELECTRODE WITH IMPROVED TEMPERATURE RESPONSE

[75] Inventors: Dominick Frollini, Jr., Trafford; Dennis G. Falconer, Gibsonia; Kenneth J. Kato, Export, all of Pa.

[73] Assignee: Allied Corporation, Morris Township, Morris County, N.J.

[21] Appl. No.: 823,989

[22] Filed: Jan. 31, 1986

Related U.S. Application Data

[63] Continuation of Ser. No. 670,855, Nov. 13, 1984, abandoned.

[51] Int. Cl.⁴ .................................... G01N 27/30
[52] U.S. Cl. ............................ 204/408; 204/414; 204/420; 204/433; 324/438
[58] Field of Search ............... 204/433, 420, 1 H, 414, 204/408; 324/438

[56] References Cited

U.S. PATENT DOCUMENTS

| | | |
|---|---|---|
| 2,977,293 | 3/1957 | Ingold ............................ 204/1 |
| 3,103,480 | 9/1963 | Watanabe et al. ............ 204/420 |
| 3,957,612 | 5/1976 | Niedrach et al. ............. 204/414 |
| 4,012,308 | 3/1977 | Jerrold-Jones et al. ...... 204/420 |
| 4,105,509 | 8/1978 | Jungck ...................... 204/414 X |
| 4,282,081 | 8/1981 | Arrance ..................... 204/414 X |
| 4,401,548 | 8/1983 | Brezinski .................. 204/420 X |
| 4,406,766 | 9/1983 | MacDonald ................. 204/433 |
| 4,477,330 | 10/1984 | Nielsen ...................... 204/414 |

FOREIGN PATENT DOCUMENTS

| | | | |
|---|---|---|---|
| 2045940 | 11/1980 | United Kingdom | 324/438 |
| 2088565 | 6/1982 | United Kingdom | 204/420 |

Primary Examiner—G. L. Kaplan
Attorney, Agent, or Firm—Alan M. Doernberg

[57] ABSTRACT

A combination pH/reference electrode is provided with the two electrochemical references being symetrically thermally insulated from the sensing membrane and being thermally adjacent each other. The portion of the pH fill buffer in contact with the inner surface of the sensing membrane is thermally insulated, as by KCl crystals, to rapidly equilibrate in temperatures with the sample solution.

10 Claims, 3 Drawing Figures

FIG. 2
FIG. 3
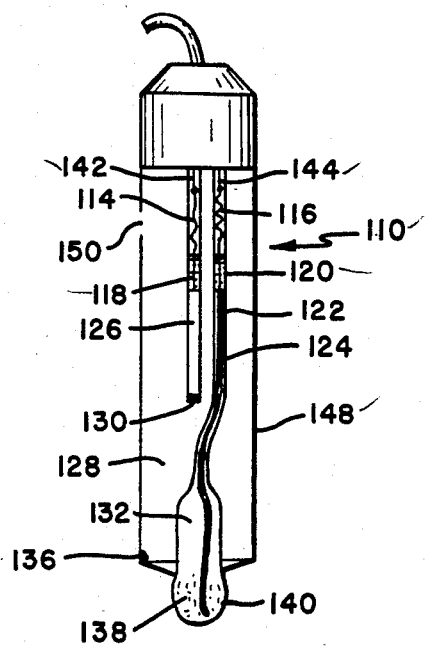
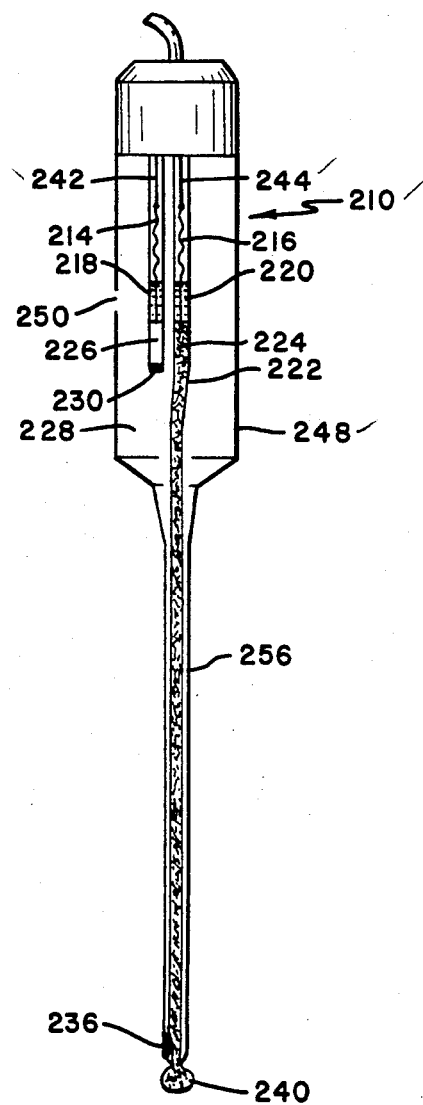

COMBINATION PH/REFERENCE ELECTRODE WITH IMPROVED TEMPERATURE RESPONSE

This application is a continuation of application Ser. No. 670,855 filed Nov. 13, 1984 and now abandoned.

The present invention relates to a combination pH electrode adapted for obtaining a stable, accurate voltage to be attained quickly with sample of widely varying temperature.

Combination pH/reference electrodes are known, containing both the glass sensing membrane and internal reference on a pH electrode and the external reference and junction or junctions of the reference electrode. Such combination electrodes have generally been designed with easily distinguishable pH electrode partners and reference electrode partners, having the characteristics of the separate annulus. In such a case, potentials attributable to each separate electrode must be considered and compensated for in the same manner as if two seaparate electrodes were being used. One particular error requiring such compensation is that due to changes in the temperature of the sample solution.

When a combination electrode, or a separate pH and reference electrode, are placed in a solution of different temperature, the entire electrode system must generally equilibrate to the single temperature before a stable reading is available. Only then will the pH electrode system give a voltage characteristic of the pH in the sample. The temperature of the sample is measured and the pH meter uses that temperature in determining a pH from the measured voltage. A product of Orion Research seeks to compensate for this by using an iodide/triodide redox reference system.

BRIEF DESCRIPTION OF THE PRESENT INVENTION

In the combination electrode of the present invention, the internal and external references within the outer body are symetrically thermally isolated from the sample and the glass membrane, but are thermally adjacent to each other. The portion of the saturated buffered salt solution in contact with the interior of the glass membrane is thermally insulated from the interior of the outer body so as to rapidly equilibrate in temperature with the sample solution outside the glass membrane. These features, based upon designing the combination electrode as a single device, enable a stable, accurate voltage to be attained quickly regardless of the temperature of the sample solution.

Accordingly, the present invention includes an electrode structure for pH measurements which combines indicator and reference electrode functions, consisting of an outer annular space containing an electrochemical reference electrically connected to the sample solution through at least one junction, and an inner annular space containing a second electrochemical reference in contact with a pH fill buffer, the pH fill buffer being in contact with the sensing membrane formed at the end of the inner annular space, characterized by the first and second electrochemical references being thermally insulated from the sensing membrane and being thermally adjacent to each other. In addition, the portion of the pH fill buffer in contact with the inner surface of the sensing membrane is thermally insulated from the interior of the inner body so as to rapidly equilibrate in temperature with the sample solution outside the sensing membrane while simultaneously exhibiting constant pH over the temperature range wherein the measurements are to be taken.

BRIEF DESCRIPTION OF THE DRAWINGS

FIG. 2 is a cross-sectional view similar to FIG. 1 of an assembly according to a second embodiment of the invention employing a standard glass body.

FIG. 3 is a cross-sectional view similar to FIG. 1 of an assembly according to a second embodiment of the invention of FIG. 1 employing a microprobe glass body.

DETAILED DESCRIPTION

Figure 1:
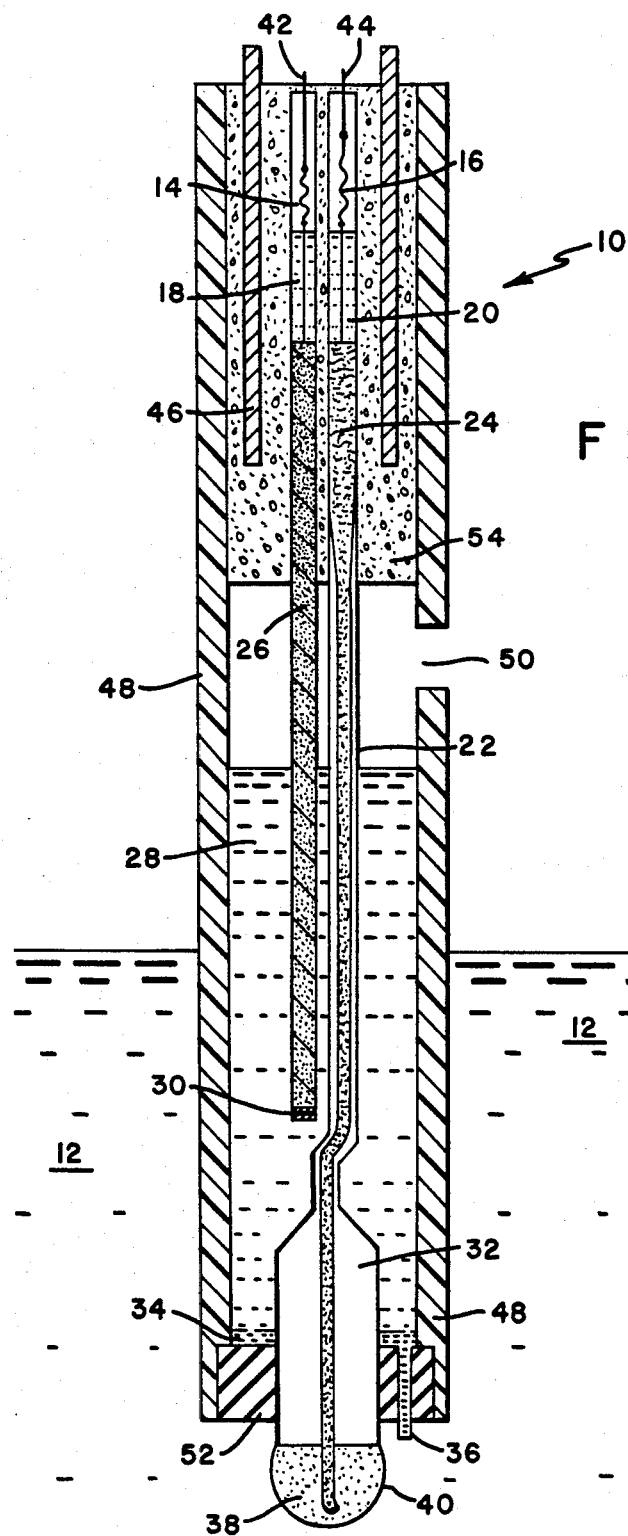
FIG. 1 is a cross-sectional view through a combination pH/reference electrode assembly of a first embodiment of the present invention.

As a preferred embodiment of the present invention, the first and second electrochemical references are each silver metal in contact with an aqueous solution of AgCl and an alkali metal chloride, wherein the preferred alkali metal chloride is KCl. Both electrochemical reference elements should be identical in construction and location within their separate compartments, where they are preferably encased in a block of insulating potting material within the upper portion of the outer body. The insulating potting material serves a dual purpose in that it holds the reference elements within the upper portion of the electrode, equidistant from the outer body and, in addition, uniformly insulates both electrochemical reference elements which ensures, to a high degree of accuracy, that the thermal gradients along the two electrodes are as nearly matched as possible. It should be appreciated, however, that such thermal insulation is not intended to be complete as in U.S. Pat. No. 4,406,766 to MacDonald. These novel features guarantee a symmetrical response to temperature changes which provide for a pH electrode that is free of temperature hysteresis and with which exact and reproducible measurements can be made under conditions of varying or elevated temperatures.

The invention includes, in some forms, a double junction reference electrode wherein the external reference electrode contained in the outer annular space makes electrical contact with the electrolyte in the outer annular space through a tube filled with a gelled electrolyte. The desirable electrolyte within the outer annular space is a saturated alkali metal chloride solution employed vicariously for AgCl/saturated KCl, in combination with the double junction reference electrode, to forestall the problems of a clogging from silver ion precipitation.

The sensing means of the present invention comprises a bulb extending through the base of the outer body, the glass sensing membrane being on the surface of the bulb outside of the outer body, wherein the bulb containing a buffered salt solution also contains at least one alkali metal chloride. The special buffered salt solution is saturated in alkali metal chloride and the bulb may contain, as a preferred form of one of the novel features, crystals of the alkali metal chloride in sufficient quantity to thermally insulate the portion of the saturated buffer solution in contact with the interior of the sensing membrane from the interior of the inner body. Such a use of KCl crystals is described for a pH electrode in U.S. Pat. No. 2,977,293 to Ingold. In addition, the pH buffer solution exhibits substantially constant pH as a function of temperature, which enables the system to display no response slow down with wide variations in temperature. The electrode further comprises a wick extending from adjacent the sensing membrane to adjacent the inner reference element to provide continuous ionic conduction between the sensing membrane and the internal reference element.

These and other features of the invention will become apparent when the following description proceeds in particular reference to the application drawings.

FIG. 1 illustrates a first embodiment of the present invention. The combination pH/reference electrode 10, with rugged outer polymer body 48, is employed for determining the pH of a sample solution 12 rapidly and accurately whereby the temperature of said sample solution ranges from $-5°$ to $100°$ C. therein. The solution at 12 may be, for example, a solution contained within a pipe at a refinery, mud found in effluent and soil testing, or a hot food slurry contained within a holding tank at a food processing center.

The present apparatus is characterized by two electrochemical references, comprising two Pt/Ag wires 14 and 16, connected at their upper end to leads 42 and 44 respectively that pass through the top of the apparatus 10 to an external circuit for potential measurement. At its lower end, the Pt/Ag wire 14 enters and remains within a Ag/AgCl/KCl pack 18, which forms the external reference in a saturated KCl solution. The Pt/Ag wire 16 enters and remains within a Ag/AgCl/KCl pack 20 as the internal reference which is filled with a pH buffer saturated KCl solution.

The lower end of the external reference pack 18 is connected with a gelled electrolyte 26 and microporous barrier 30, which forms a channel of ionic contact between the junction electrolyte 28 and the external reference pack 18. The overall configuration is therefore a double junction reference electrode. The junction electrolyte 28 is a saturated aqueous alkali metal chloride solution employed vicariously for AgCl/saturated KCl, in combination with the double junction references electrode, to forestall the problems of clogging from silver ion precipitation. The lower end of the Ag-/AgCl/KCl internal reference pack 20 is sealed atop the upper end of the housing tube 22, and a wicking material 24 fills the housing tube 22 to provide continuous ionic conduction between the sensing membrane 40 and the internal reference element 20.

When the combination pH/reference electrode 10 is immersed in the sample solution 12 and both reference electrodes are electrically connected to an external circuit by conductors 42 and 44, the potential across the glass membrane 40 changes in proportion to the difference in the pH between the sample solution 12 and a special pH buffer solution 32. Such special pH buffer solution 32 is contained within the sensing membrane 40. Two exemplary compositions for the pH buffer solution are: (a) one molar acetic acid, one molar sodium acetate and KCl to the point of saturation, and (b) water which is 0.157 molar in boric acid, 0.3937 molar in succinic acid, 0.03937 molar in sodium sulfate and 0.06063 molar in borax and which is then saturated with KCl. Such a pH buffer solution 32 exhibits substantially constant pH as a function of temperature, which enables the system to display no response slow down with wide variations in temperature. The difference in potential between the sample solution 12 and the contact 44 for the internal reference element 20 changes with pH, and it is this change in potential that is to be monitored. The role of the external reference element 18 is to establish a fixed half-cell potential between the sample solution 12 and contact 42 for the external reference element 18. This action can be initiated by immersing the external reference element 18 in known electrolyte solution, specifically the saturated KCl solution 28, and then establishing electrical contact between this electrolyte and the sample solution 12 by way of a reference junction 36. The junction electrolyte 28 can be added through an inlet hole 50 and is maintained as a saturated solution with excess KCl crystals 34 which settle atop of the silicon rubber bung 52 situated at the base of the apparatus.

A primary advantage of the present invention is the fast and accurate electrode response made possible, in part, by the portion of the saturated buffered salt solution 32 and excess KCl crystals 38 in contact with the interior of the sensing membrane 40, which is thermally insulated from the interior of the outer body so as to rapidly equilibrate in temperature with the sample solution 12 outside the sensing membrane 40. The construction of the preferred embodiment of the invention, whereby the reference elements 18 and 20 are identical in construction and location, relative to the outer polymer body 48, also ensures to a high degree a symmetrical response to temperature changes and as a result exhibits virtually no hysteresis upon temperature cycling. In addition, both electrochemical references 18 and 20 are encased in a block of insulating potting material 54 and surrounded by an electrical shield 46 which further ensures an accurate voltage to be attained quickly regardless of the temperature of the sample solution 12.

It will be apparent to those skilled in the art that numerous variations and modifications may be made in the preferred embodiment of the invention described above. Such is the case with the combination pH/reference electrodes 110 and 210 of FIG. 2 and FIG. 3 which are designed with a glass outer body 148 and 248 respectively in place of the polymer outer body 48 employed in the electrode of FIG. 1. Other variations in the apparatus which become evident in both FIG. 2 and FIG. 3 are the relative positions of the two pairs of electrochemical references 142 and 144, and 242 and 244 which are no longer encased within the block of insulating potting material 54 nor surrounded by the electrical shield 46. In the electrode illustrated in FIG. 2 both electrochemical references 118 and 120 have been transferred from the uppermost portion of the electrode to the lower portion of apparatus in close proximity to the sample solution 12. In addition, a change in the overall length of the electrode has occured in order to render the present invention better adaptable to a broader range of applications. These modifications of the apparatus, including a shift in position of the electrochemical references 118 and 120 and the curtailment of the overall length of the electrode, however, do not distract from a primary objective of the invention, which is to supply a symmetrical response to temperature changes and as a result exhibit virtually no hystersis upon temperature cycling.

The other numerals in FIG. 2 referring to elements of electrode 110 (114, 116, 122, 126, 128, 130, 132, 136, 138, 140 and 150) indicate elements identical or substantially identical to the corresponding elements (14, 16, 22, 24, 26, 28, 30, 32, 36, 38, 40 and 50, respectively) of electrode 10 in FIG. 1.

Similarly, the electrode illustrated in FIG. 3 has undergone several visual alteration which include a narrowing of the outer body diameter 256 just beneath the reference junction 230 of the double junction electrode, and the curtailment of the overall length of the double junction electrode. A primary objective for the transformation of the diameter of the outer body 256 was to provide the user with a combination pH/reference electrode 210 with the capability of determining the pH of a solution in difficult to reach localities.

The other numerals in FIG. 3 referring to elements of electrode 210 (214, 216, 222, 224, 226, 228, 230, 232, 236, 238, 240 and 250) indicate elements identical or substantially identical to the corresponding elements (14, 16, 22, 24, 26, 28, 30, 32, 36, 38, 40 and 50, respectively) of electrode 10 in FIG. 1.

We claim:

1. An electrode structure for pH measurements at a variety of temperatures within a temperature range which combines indicator and reference electrode functions, consisting of an outer annual space containing an electrochemical reference electrically connected to the sample solution through a secondary electrolyte and at least one junction, and an inner annular space containing a second electrochemical reference in contact with a pH fill buffer, the pH fill buffer being in contact with a sensing membrane formed at the end of the inner annular space, characterized by:
   (a) the first and second electrochemical references being thermally insulated from the sensing membrane sufficiently to have matched thermal gradients when the temperature of the sample solution outside of the sensing membrane changes and being in thermal communication with each other;
   (b) that portion of the pH fill buffer in contact with the inner surface of the sensing membrane being thermally insulated by salt crystals covering the interior of the sensing membrane from the remainder of the pH fill buffer so that the portion can rapidly equilibrate in temperature with the sample solution outside the sensing membrane;
   (c) the pH fill buffer solution exhibiting substantially constant pH over a temperature range of $-5°$ C. to $100°$ C.

2. The combination electrode of claim 1 wherein the first and second electrochemical references are each silver metal in contact with an aqueous solution of AgCl and an alkali metal chloride.

3. The combination electrode of claim 2 wherein said alkali metal chloride is KCl.

4. The combination electrode of claim 1 wherein the reference electrode contained in the outer annular space makes electrical contact to the electrolyte in the outer annular space through a tube filled with a gelled electrolyte.

5. The combination electrode of claim 4 wherein the secondary electrolyte is a saturated aqueous alkali metal chloride solution within the outer annular space.

6. The combination electrode of claim 1 comprising a bulb extending through the base of said outer body, the sensing membrane being on the surface of said bulb outside said outer body, said bulb containing said buffered salt solution which contains at least one alkali metal chloride.

7. The combination electrode of claim 1 wherein the first and second electrochemical references are encased in a block of insulating material within the upper portion of the outer body.

8. The combination electrode of claim 1 wherein the first and second electrochemical references occupy a common diameter line and are each equally radially spaced along said common diameter line from the outer body of the electrode.

9. The combination electrode of claim 1 wherein the reference elements are identical in construction and symmetrically similar in location within their separate compartments.

10. The combination electrode of claim 1 further comprising a wick extending from adjacent the sensing membrane to adjacent the inner reference element.

* * * * *